United States Patent [19]
Draber et al.

[11] 3,934,014
[45] Jan. 20, 1976

[54] N-METHYL-IMIDAZOLE DERIVATIVES AS ANTI-MYCOTIC AGENTS

[75] Inventors: Wilfried Draber; Karl Heinz Büchel; Erik Regel; Manfred Plempel, all of Wuppertal-Elberfeld, Germany

[73] Assignee: Bayer Aktiengesellschaft, Germany

[22] Filed: May 31, 1974

[21] Appl. No.: 474,873

Related U.S. Application Data

[62] Division of Ser. No. 310,423, Nov. 29, 1972.

[30] Foreign Application Priority Data
Mar. 23, 1970 Germany.......................... 2013793

[52] U.S. Cl. ................................................ 424/251
[51] Int. Cl.² ........................................ A61K 31/505
[58] Field of Search .................................... 424/251

[56] References Cited
UNITED STATES PATENTS
3,048,587  8/1962  Oroshnik .......................... 260/256.4
3,381,015  4/1968  Shen et al. ........................... 260/295

Primary Examiner—Jerome D. Goldberg

[57] ABSTRACT

N-methyl-imidazole derivatives of the formula:

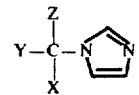

or a pharmaceutically acceptable non-toxic salt thereof, wherein
X is an unsubstituted or substituted 6-membered heteroaromatic moiety having two nitro heteroatoms,
Y is an unsubstituted or substituted aliphatic moiety, an unsubstituted or substituted cycloaliphatic moiety, an unsubstituted or substituted aralkyl moiety or an unsubstituted or substituted aryl moiety, and
Z is an unsubstituted or substituted aliphatic moiety, an unsubstituted or substituted cycloaliphatic moiety, an unsubstituted or substituted aralkyl moiety, an unsubstituted or substituted aryl moiety, an unsubstituted or substituted pyridyl moiety or an alkoxycarbonyl moiety, are useful as antimycotic agents.

16 Claims, No Drawings

N-METHYL-IMIDAZOLE DERIVATIVES AS ANTI-MYCOTIC AGENTS

This is a division of application Ser. No. 310,423 filed Nov. 29, 1972.

The present invention is concerned with N-methyl-imidazole derivatives and their production as well as with pharmaceutical compositions, wherein said N-methyl-imidazole derivatives are the active ingredient and with methods of treating mycotic infections which comprises administering the N-methyl-imidazole derivatives of the present invention.

More particularly, the present invention is concerned with N-methyl-imidazole derivatives which are substituted at the methyl carbon atom by a 6-membered heterocyclic moiety having two ring nitrogen atoms. These compounds are particularly useful for their anti-mycotic and fungitoxic activity.

Some derivatives of 6-membered heterocyclic compounds, which contain two nitrogen atoms in the nucleus, are known. U.S. Pat. No. 2,839,446 describes pyrimidies which carry a trichloromethylsulphonyl group in the 2-position as being leaf fungicides. Netherlands Patent Specification 6,806,106 describes 5-substituted pyrimidines carrying a disubstituted or trisubstituted methyl group as the substituent, it being possible for one of the substituents on this methyl group to be a hydroxyl, amino or phenylamino group. The pyrimidyl-diaryl-carbinols, in particular, represent valuable systematic plant fungicides. These previously known compounds are however all exclusively active against plantpathogenic fungi and bacteria.

N-trityl-imidazole and substituted N-trityl-imidazoles are referred to in U.S. Pat. No. 3,321,366 as being useful against plant fungi.

The compounds of the present invention may be represented by the formula:

wherein
X is an unsubstituted or substituted 6-membered heteroaromatic moiety having two nitro heteroatoms,
Y is an unsubstituted or substituted aliphatic moiety, an unsubstituted or substituted cycloaliphatic moiety, an unsubstituted or substituted aralkyl moiety or an unsubstituted or substituted aryl moiety, and
Z is an unsubstituted or substituted aliphatic moiety, an unsubstituted or substituted cycloaliphatic moiety, an unsubstituted or substituted aralkyl moiety, an unsubstituted or substituted aryl moiety, an unsubstituted or substituted pyridyl moiety or an alkoxycarbonyl moiety,
and include pharmaceutically acceptable non-toxic salts thereof.

Among the heteroaromatic moieties for X are those of the formula:

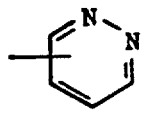 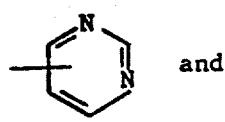 and 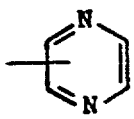

which are bonded to the central carbon atom of formula (I) via a carbon atom in the ring and can either by unsubstituted or may be substituted by 1 to 3, and preferably 1 or 2 substituents which can either be the same or different. Suitable substituents include halogen, particularly fluorine, chlorine and bromine, and especially chlorine, alkyl of 1 to 4 carbon atoms, and preferably 1 or 2 carbon atoms, alkoxy of 1 to 4 carbon atoms, and preferably 1 or 2 carbon atoms or phenyl. Among the above alkyl and alkoxy substituents are methyl, ethyl, n-propyl, isopropyl, n-butyl, isobutyl, tert. butyl, particularly methyl and ethyl, and methoxy, ethoxy, n-propoxy, isopropoxy, n-butoxy, isobutoxy and tert. butoxy, especially methoxy and ethoxy. If X is a pyridazine ring, it is preferably bonded in the 4-position to the central carbon atom. If R is a pyrimidine ring, it is preferred that it be bonded in the 2- or 5-position to the central carbon atom.

When Y and/or Z are unsubstituted or substituted aliphatic moieties, it is preferred that such aliphatic moieties by straight or branched chain alkyl of 1 to 6 carbon atoms, and especially 1 to 4 carbon atoms, particularly methyl, ethyl, n-propyl, isopropyl, n-butyl, iso-butyl and tert. butyl, particularly methyl and tert. butyl. When such aliphatic moieties are substituted, it is preferred that there be one or more substituents, and preferably one or two substituents. Suitable substituents are alkyl of 1 to 4 carbon atoms, and preferably 1 or 2 carbon atoms, alkoxy of 1 to 4 carbon atoms, and preferably 1 or 2 carbon atoms, thioalkyl of 1 to 4 carbon atoms, and preferably 1 or 2 carbon atoms, trifluoromethyl, halogen, especially fluorine, chlorine or bromine, nitro and cyano. Particular alkyl, alkoxy and thioalkyl moieties include methyl, ethyl, methoxy, ethoxy, methylmercapto, i.e. thiomethyl and ethylmercapto, i.e. thioethyl.

When X and/or Z are unsubstituted or substituted cycloaliphatic moieties, it is preferred that these have 3 to 8 carbon atoms, and especially 3 to 6 carbon atoms. Cyclopropyl and cyclohexyl are preferred moieties. When the cycloaliphatic moieties are substituted, it is preferred that there are one or more substituents and preferably one or two substituents. Suitable substituents include alkyl of 1 to 4 carbon atoms, preferably 1 or 2 carbon atoms, alkoxy of 1 to 4 carbon atoms, preferably 1 or 2 carbon atoms, thioalkyl of 1 to 4 carbon atoms, preferably 1 or 2 carbon atoms, trifluoromethyl, halogen, especially fluorine, chlorine or bromine, nitro and cyano. Among the alkyl, alkoxy and thialkyl moieties are methyl, ethyl, methoxy, ethoxy, methylmercapto and ethylmercapto.

When Y and/or Z are unsubstituted or substituted aralkyl moieties, it is preferred that these have 6 to 12 carbon atoms, and especially 6 carbon atoms in the aryl portion, and 1 to 4 carbon atoms, and especially 1 or 2 carbon atoms in the alkyl portion. Benzyl and p-chlorobenzyl are among the preferred substituents. When the aralkyl moiety is substituted, there can be one or more substituents, preferably one or two. Substituents include alkyl of 1 to 4 carbon atoms, preferably 1 or 2 carbon atoms, alkoxy of 1 to 4 carbon atoms, preferably 1 or 2 carbon atoms, thioalkyl of 1 to 4 carbon atoms, preferably 1 or 2 carbon atoms, trifluoromethyl, halogen, especially fluorine, chlorine or bromine, nitro and cyano. Among the alkyl, alkoxy and thialkyl moieties are methyl, ethyl, methoxy, ethoxy, methylmercapto and ethylmercapto.

When Y and/or Z are unsubstituted or substituted aryl moieties, it is preferred that these have 6 to 10 carbon atoms, and especially 6 carbon atoms. When the aryl moiety is substituted, there can be one or more substituents, preferably 1 or 2. Substituents include alkyl of 1 to 4 carbon atoms, preferably 1 or 2 carbon atoms, alkoxy of 1 to 4 carbon atoms, preferably 1 or 2 carbon atoms, thioalkyl of 1 to 4 carbon atoms, preferably 1 or 2 carbon atoms, trifluoromethyl, halogen, especially fluorine, chlorine or bromine, nitro and cyano. Among the alkyl, alkoxy, and thioalkyl moieties are methyl, ethyl, methoxy, ethoxy, methylmercapto and ethylmercapto.

The preferred aryl moieties are phenyl, p-fluorophenyl, o-chlorophenyl, o-methylphenyl, o-isopropylphenyl, p-methoxyphenyl, m-trifluoromethylphenyl, m-nitrophenyl and naphthyl.

When Z is an unsubstituted or substituted pyridyl moiety, the pyridyl moiety is bonded in the 2-, 3- or 4-position to the central carbon atom. When the pyridyl moiety is substituted, it can contain one or more substituents, and preferably 1 or 2 substituents. Suitable substituents include alkyl of 1 to 4 carbon atoms, preferably 1 or 2 carbon atoms, alkoxy of 1 to 4 carbon atoms, preferably 1 or 2 carbon atoms, thioalkyl of 1 to 4 carbon atoms, preferably 1 or 2 carbon atoms, trifluoromethyl, halogen, especially fluorine, chlorine and bromine, nitro and cyano. Among the alkyl, alkoxy and thioalkyl moieties are methyl, ethyl, methoxy, ethoxy, methylmercapto and ethylmercapto. When Z is pyridyl, it is preferred that the pyridyl moiety be unsubstituted.

When Z is alkoxycarbonyl, it is preferred that there be 1 to 4 carbon atoms, and especially 1 or 2 carbon atoms, in the alkyl moiety. Methoxycarbonyl and ethoxycarbonyl are preferred.

Preferred salts of the compounds of the present invention are those which are formed with pharmaceutically acceptable non-toxic acids, i.e. those which are physiologically well tolerated. Examples of such acids are the hydrogen halide acids, such as for example hydrobromic acid and hydrochloric acid, phosphoric acids, sulphonic acids, monocarboxylic and dicarboxylic acids and hydroxycarboxylic acids. As examples of organic acids, acetic acid, tartaric acid, lactic acid, malic acid, citric acid, salicylic acid, sorbic acid and ascorbic acid may be mentioned.

Particularly preferred compounds are those of the formula (I) in which

X is a 6-membered heteroaromatic ring of the formula:

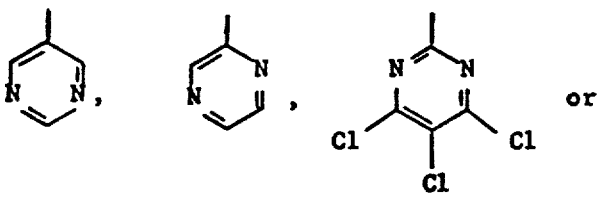

Y is phenyl or p-fluorophenyl, and
Z is phenyl and pharmaceutically acceptable non-toxic salts thereof.

The compounds of the present invention can be produced according to several processes. According to one process, the compounds of the present invention are produced if a. a compound of the formula

wherein
X, Y and Z are as above defined, and
Hal is Cl or Br, is reacted with imidazole, optionally in the presence of an acid acceptor or in the presence of an excess of imidazole in a polar organic solvent at temperatures between about 20° and about 150° C, and the salt is optionally manufactured, or b. a carbinol of the formula:

wherein
X, Y and Z are as above defined,
is reacted with thionyldiimidazole of formula

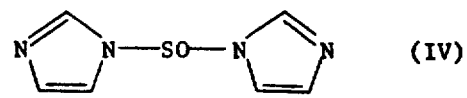

in an aprotic solvent, and the salt is optionally manufactured.

The starting compounds required for the manufacture of the new compounds (I) are known or are obtainable according to known processes.

The compounds (II) can be manufactured in various ways. For example, it is possible to start from a carbinol (III) and to react this with a halogenating agent, such as for example thionyl chloride, thionyl bromide, phosphoryl chloride, phosphoryl bromide, acetyl chloride or acetyl bromide, in solvents, such as for example ether, methylene chloride, benzene or toluene. It may at times also be appropriate to carry out the halogenation in a polar solvent and to follow this directly by the reaction with imidazole, without intermediate isolation of the halide formed. As polar organic solvents, acetonitrile nitromethane, dimethylformamide or hexamethylphosphoric acid triamide may for example be mentioned.

A further process for the manufacture of compounds of the formula (II), in which Hal is chlorine and X and Y are as above defined, comprises reacting a ketone of the formula:

in which

X and Y are as above defined, firstly with PCl₅ to give a dichloride of the formula:

wherein X and Y are as above defined.

This dichloride is subsequently reacted with an optionally substituted aromatic compound, in the presence of at least one equivalent of aluminium chloride, to give the chloride (II).

An excess of the aromatic compound, or some other solvent suitable for this reaction, such as for example carbon disulphide, can be used as the solvent in this Friedel-Crafts reaction.

A further process for the manufacture of the halides (II) consists of reacting a methane derivative of the formula

in which

X, Y and Z have the abovementioned meaning, with a halogenating agent which operates by a radical mechanism, such as for example N-chlorophthalimide or N-bromosuccinimide, in an inert organic solvent, such as for example carbon tetrachloride.

The starting substances required for the processes indicated are known or can be manufactured analogously to known processes. For example, 2-diphenyl-methylpyrazine is obtained according to a method described by Behun et al., J. Org. Chem. 26, 3379 (1961). Further pyrazylcarbinols have been described by Hirschberg, J. Heterocyclic Chem. 2, 209 (1965). Further, pyrazine derivatives which can be used as starting substances of general formulae (II), (III) and (VII), in which X represents a pyrazine radical, for the manufacture of compounds of formula (I), in which X is a pyrazine radical, are described in Netherlands Patent Specification 105,432 and in German Displayed Specification 1,913,726.

Pyrimidine compounds of the formula (II), (III) and (VII), in which X is pyrimidine, used as starting substances, are also known or can be manufactured according to processes which are in themselves known. Several processes are for example given in Chem. Ber. 93, 230 (1960) and in Netherlands Patent Application 6,806,106.

Pyridazine compounds of the formula (II), (III) and (VII), in which X is pyridazine, can also be obtained in an analogous manner to that described in the abovementioned publications.

In process variant (a) the starting compound (II), the imidazole and the acid acceptor are employed in about molar amounts. If an excess of imidazole is added as the acid acceptor, about 2 mols of imidazole must be used for this reaction. The reaction temperature is about 20° to about 150°C, preferably about 60° to about 100°C.

As solvents in process (a), polar organic solvents, such as for example lower alkylnitriles, such as for example acetonitrile, dimethylformamide, dimethylsulphoxide, lower alkylketones, such as for example diethyl ketone, and hexamethyl phosphoric acid triamide can be used.

Inorganic and organic bases can serve as acid acceptors. As inorganic bases, the alkali carbonates and alkaline earth carbonates, especially potassium carbonate and calcium carbonate, may for example be used. As organic bases, lower alkylamines, such as for example triethylamine, as well as hetero-aromatic bases, such as for example pyridine and lutidine may for example be used.

In process variant b), the reactants (III) and (IV) are employed in about molar amounts. Preferably, however, about 1 to about 2 mols of thionyldiimidazole (IV) are employed per 1 mol of carbinol (III). The reaction temperature is about 0 to about 100°C, preferably about 20° to about 50°C.

The reaction (b) is generally carried out in inert organic solvents, such as for example lower alkylnitriles, such as for example acetonitrile, ethers, such as for example tetrahydrofurane and diisopropyl ether, dimethylformamide or chlorinated hydrocarbons, such as for example chloroform.

If 2-isopropyl-phenyl-2-pyrazyl-carbinol is used as the starting material, the course of the reaction according to process a) can be represented by the following equation:

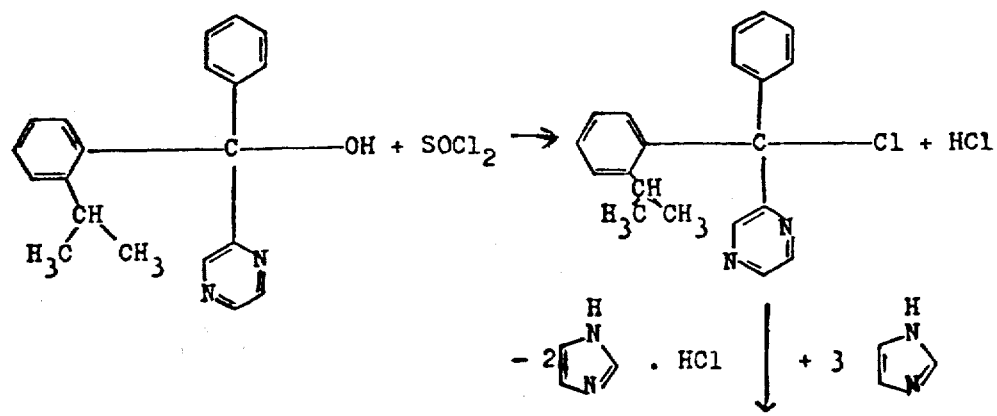

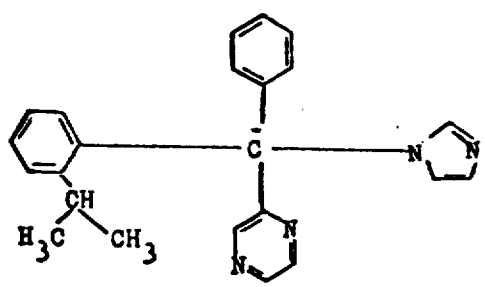

The course of the reaction of process (b) can be represented by the following equation for the example of the reaction of tert.-butyl-phenyo-5-pyrimidyl-carbinol with thionyldiimidazole:

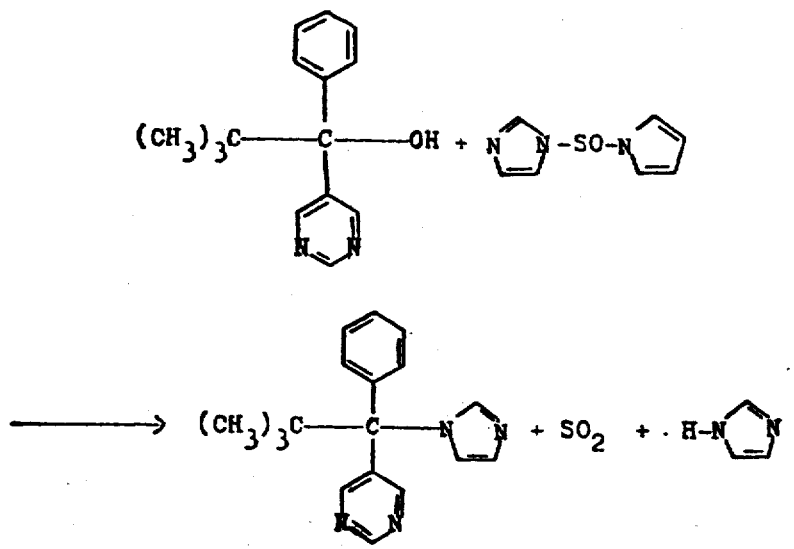

The following non-limitative examples more particular illustrate the present invention.

EXAMPLE 1

Diphenyl-pyrimid-5-yl-imidazol-1-yl-methane 26.2 g (0.1 mole) of diphenyl-pyrimid-5-yl-carbinol, melting point 161°C, are treated with a solution of 0.15 mol of thionyldiimidazole in 200 ml of dry acetonitrile and the mixture is heated to the boil for 10 minutes. Thereafter it is cooled, diluted with ice water and filtered. The residue is washed with water. 23.6 g (76% of theory) of a white, finely crystalline substance of formula

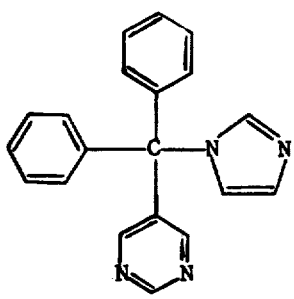

of melting point 209°C are obtained.

Analysis: $C_{20}H_{16}N_4$ (312.36) Calculated: C 76.9%; H 5.2%; N 17.9%; Found: C 77.3%; H 5.6%; N 18.0%

The thionyldiimidazole used for the reaction is obtainable as follows.

40.8 g (0.6 mol) of imidazole dried over $P_2O_5$ are suspended in 150 ml of acetonitrile distilled over $P_2O_5$ and treated, at 0°C, with 17.7 g (0.15 mol) of freshly distilled thionyl chloride. The imidazole hydrochloride which has precipitated is rapidly filtered off and rinsed with 50 ml of acetonitrile. The filtrate is immediately used for the reaction.

EXAMPLE 2

Diphenyl-pyrazyl-imidazol-1-yl-methane 26.2 g (0.1 mol) of diphenyl-pyrazyl-carbinol, melting point 111°C, are treated with a solution of 0.15 mol of thionyldiimidazole in 200 ml of dry acetonitrile and the mixture is heated under reflux for one hour. Thereafter it is concentrated and the oily-crystalline residue is washed with water. 7.2 g of a light brown crude product are obtained, which after recrystallisation from ether/acetone yield 8.8 g (28% of theory) of a compound of the formula

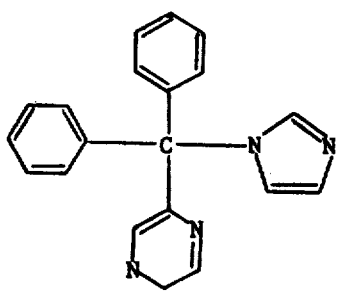

in the form of white crystals of melting point 198°C.

Analysis: $C_{20}H_{16}N_4$ (312.36); Calculated: C 76.9%; H 5.2%; N 17.9%; Found: C 76.9%; H 5.5%; N 18.0%.

EXAMPLE 3

4-Fluorophenyl-phenyl-pyrazyl-imidazol-1-yl-methane 28.0 g (0.1 mol) of 4-fluorophenyl-phenyl-pyrazyl-carbinol together with a solution of 0.15 mol of thionyldiimidazole in 200 ml of acetonitrile are heated to the boil for one hour. Thereafter the mixture is filtered and concentrated, the residue is taken up in methylene chloride and the solution is repeatedly extracted by shaking with water. The methylene chloride phase is dried and concentrated. A brown oil is obtained, which is taken up in acetonitrile. After treating the solution with active charcoal and filtering, dry hydrogen chloride is passed in until saturation is reached, and the precipitated product is filtered off and rinsed with acetonitrile and ether. 12.7 g (35% of theory) of the compound of formula

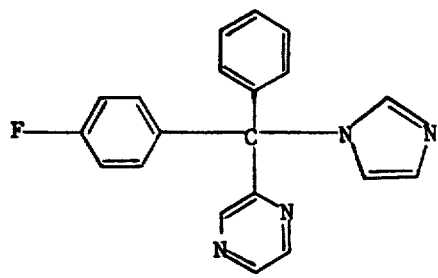

are obtained in the form of a yellow, hygroscopic powder of melting point 86°C (decomposition).

Analysis: $C_{20}H_{15}FN_4 \cdot HCl$ (366.81); Calculated: N 15.3%; Cl 9.7%; Found: N 14.8%; Cl 9.9%

EXAMPLE 4

Diphenyl-4,5,6-trichloropyrimid-2-yl-imidazol-1-yl-methane 34.0 g (0.1 mol) of diphenyl-4,5,6-trichloropyrimid-2-yl-chloromethane in 250 ml of absolute acetonitrile are stirred with 13.6 g (0.2 mol) of imidazole for 3 hours at room temperature and thereafter heated to the boil for 15 minutes. The mixture is then concentrated and the dark brown residue is washed with water and taken up in methylene chloride. After drying with sodium sulphate, treating with active charcoal and filtering, the solution is concentrated. The residue is extracted by boiling with petroleum ether, and the mixture is filtered and again concentrated. Finally, the material is recrystallised from a little acetonitrile. 17.0 g (40% of theory) of the compound of formula

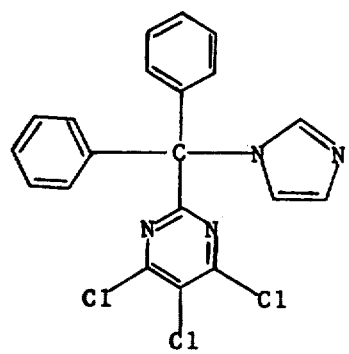

are obtained in the form of orange-coloured crystals of melting point 142° – 146° C.

EXAMPLE 5

Diphenyl-pyrimid-2-yl-imidazol-1-yl-methane 26.2 g (0.1 mol) of diphenyl-pyrymid-2-yl-carbinol are dissolved in 100 ml of absolute acetonitrile and treated with a solution of 0.15 mol of thionyldiimidazole in 200 ml of acetonitrile. The mixture is stirred for one hour at room temperature and subsequently heated to the boil for 10 minutes. It is then concentrated to about half its volume and diluted with ice water. The yellow oil which has precipitated is washed with water, taken up in methylene chloride and the solution dried. After concentration, a viscous residue remains which slowly crystallises. 16.0 g (41% of theory) of the compound of formula

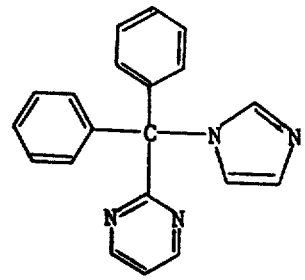

are thus obtained, having a melting point of 138° – 143° C.

The following compounds, wherein X, Y and Z of the below set forth formula are as indicated, are produced in a manner analogous to that of the preceding examples from the reactants set forth in the table which follows:

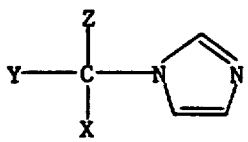

| Example No. | X | Y | Z |
|---|---|---|---|
| 6 | 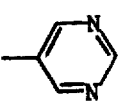 | 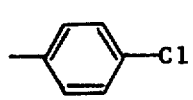 | 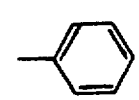 |
| 7 | 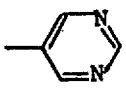 | 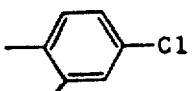 | 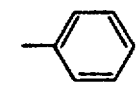 |

| Example No. | X | Y | Z |
|---|---|---|---|
| 8 | 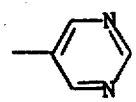 | 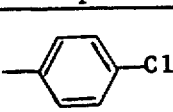 | 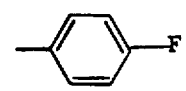 |
| 9 | 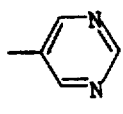 | 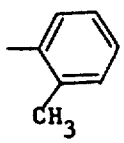 | 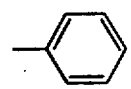 |
| 10 | 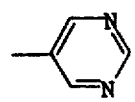 | 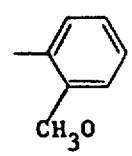 | 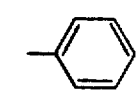 |
| 11 | 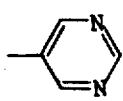 |  —C(CH$_3$)$_3$ |  |
| 12 | 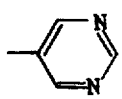 | 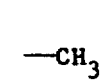 —CH$_3$ | 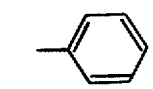 |
| 13 | 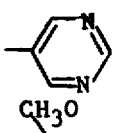 | 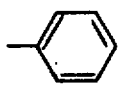 | 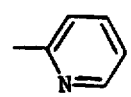 |
| 14 | 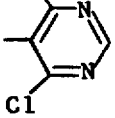 | 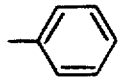 | 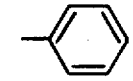 |
| 15 | 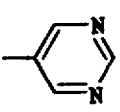 | 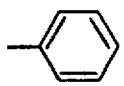 | 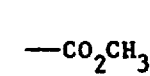 —CO$_2$CH$_3$ |
| 16 | 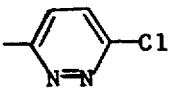 | 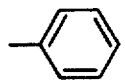 | 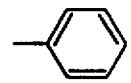 |
| 17 | 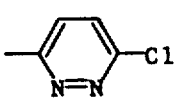 | 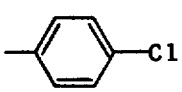 | 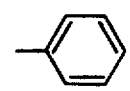 |
| 18 | 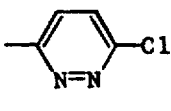 | 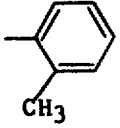 | 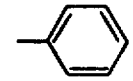 |
| 19 | 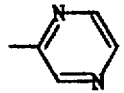 | 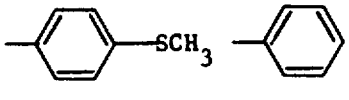 | 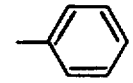 |

| Example No. | X | Y | Z |
|---|---|---|---|
| 20 | 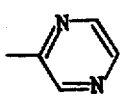 | 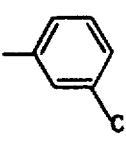 | 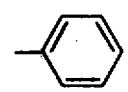 |
| 21 | 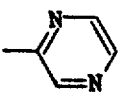 | 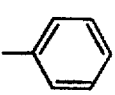 | 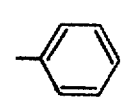 |
| 22 | 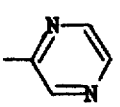 |  | 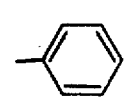 |
| 23 | 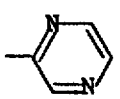 | 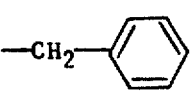 | 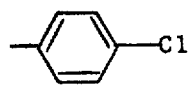 |
| 24 | 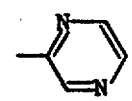 | 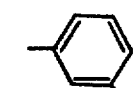 | 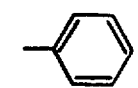 |
| 25 | 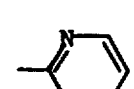 | 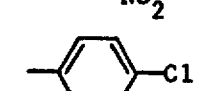 | 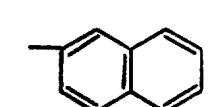 |
| 26 | 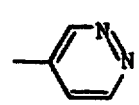 | 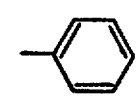 | 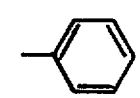 |
| 27 | 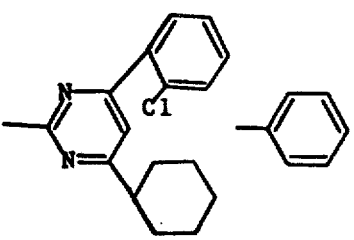 | 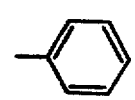 | 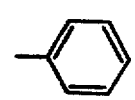 |
Table
| Example No. | process a) (see pages 7–8) reactants: | | process b) (see pages 7–8) reactants: | |
|---|---|---|---|---|
| | 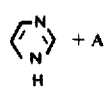 + A | | 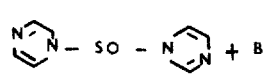 + B | |
| | A | | B | |
| 6 | 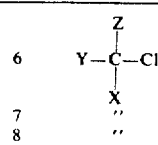 | (meaning of X,Y,Z for each example see pages 17–19) | 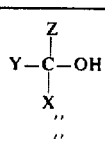 | |
| 7 | " | | " | |
| 8 | " | | " | |

Table-continued

| Example No. | process a) (see pages 7-8) reactants: imidazole + A | process b) (see pages 7-8) reactants: imidazole-SO-imidazole + B |
|---|---|---|
| | A | B |
| 9 | " | " |
| 10 | " | " |
| 11 | " | " |
| 12 | " | " |
| 13 | Y—C(Z)(X)—Br | " |
| 14 | " | " |
| 15 | " | " |
| 16 | " | " |
| 17 | " | " |
| 18 | " | " |
| 19 | " | " |
| 20 | " | " |
| 21 | Y—C(Z)(X)—Cl | " |
| 22 | " | " |
| 23 | " | " |
| 24 | " | " |
| 25 | " | " |
| 26 | " | " |
| 27 | " | " |

As already mentioned, the new compounds show an excellent anti-mycotic activity, as can be seen from the following in vitro and in vivo experiments.

a. Anti-mycotic action in vitro.

The Table summarises the anti-mycotic actions in vitro of several preparations towards several species of fungi:

| Compound from example | Minimal inhibitory concentration (MIC) in γ/ml of substrate | | | | |
|---|---|---|---|---|---|
| | Trichophyton mentagrophytes | Microsporon felineum | Candida albicans | Aspergillus niger | Penicillium commune |
| 2 | 4 | 10 | 40 | 10 | 40 |
| 1 | 4 | 40 | 40 | 10 | 100 |
| 3 | <1 | 4 | 4 | 4 | 4 |

The MIC determination was carried out in a serial dilution test, in the dilution series 100-40-20-10-4-1 γ/ml of substrate. The following were used as nutrient substrates:

a. for Dermatophytes: Sabouraud's test medium
b. for yeasts: meat water - glucose - bouillon.

The incubation temperature was 28°C, and the incubation time was 24 to 96 hours.

The preparations are primarily fungistatic: fungicidal effects can be achieved in vitro with 4-fold to 6-fold higher MIC concentrations.

The in vitro experiments were also carried out with the compounds from examples 1, 2 and 3, which can be regarded as representative of the entire class of compounds.

b. Anti-mycotic action in vivo.

1. Experimental canidosis in mice.

White mice — strain $CF_1$-SPF, pellet fodder, water ad libitum — were each intravenously infected with 1 – 5 × $10^6$ *Candida albicans* cells. Untreated control animals died 3 to 6 days after infection to the extent of 95% from uraemia through multiple abscess formation in the kidneys.

In the case of oral and/or parenteral therapy with the preparations mentioned — especially with the compound from example 3 — in daily doses of 50 to 200 mg/kg of body weight, divided into two individual doses, 60 to 90% of the animals survived on the 6th day after the infection. In these experiments, the therapy was started on the day of the infection and continued up to the 5th day after infection.

The preparations are rapidly resorbed after oral administration. Blood level maxima, with concentrations of up to 6 γ/mg of serum, are reached 4 to 5 hours after administration.

2. Experimental trichophytia in mice, caused by *Trichophyton Quinckaenum*.

White $CF_1$-SPF mice were infected dorsally with a spore suspension of *Trichophyton Quinckeanum*. After 8 to 10 days typical, multiple cups developed in the untreated control aminals.

By means of daily doses of 50 to 200 mg/kg of body weight, divided into two individual doses and administered orally from the day of infection up to the 8th day after infection, it was possible completely to suppress the occurrence of the cups typical of the infection in infected animals.

3. Experimental trichophytia in guinea pigs caused by *Trichophyton mentagrophytes*.

Guinea pigs — Pearlbright white, weighing 400 to 500 g, m were infected on their shaved back with a spore suspension of *Trichophyton mentagrophytes*. A deep dermatomycosis developed at the point of infection within 21 to 25 days, and continued up to the 30th – 34th day after infection.

In the case of animals which were treated locally with a 1% strength solution of the preparations in polyethylene glycol 400, once daily from the 3rd day after infection to the 14th day after infection, the infection completely healed within the therapy time. Non-tolerance reactions by the skin were not observable in these experiments.

According to these results, the preparations mentioned can be regarded as good anti-mycotic agents of broad activity, which are curatively active both in oral and parenteral administration and in local administration in animal experiments.

The excellent anti-mycotic activity of the new compounds makes it possible to employ them in the whole of human medicine and veterinary medicine.

The following are envisaged as indications for the new preparations:

1. in human medicine:

Dermatomycoses by Dermatophytes, for example varieties of Trichophyton, Microsporon and Epidermophyton, systemic and organic mycoses by, for example, varieties of Candida, Histoplasma, Cryptococcus and Coccidioides, Aspergilli and other moulds.

2. in veterinary medicine:

Dermatomycoses as well as organic mycoses and systemic mycoses caused by Dermatophytes, yeasts, biphase fungi and moulds.

The new compounds can be administered orally, parenterally or locally, as free bases or in the form of their salts with physiologically tolerated acids.

In general, it has proved advantageous to administer amount of about 30 mg to about 200 mg, preferably about 50 to 100 mg, per kg of body weight per day, to achieve effective results. Nevertheless it can at times be necessary to deviate from the amounts mentioned, in particular depending on the body weight of the test animal or patient, the nature of the method of administration, and severity of the condition as well as because of the species of animal and its individual behavior towards the medicine, or the patient's past medical history, or the nature of the formulation and the point in time or interval at which the administration takes place. Thus it can suffice in some cases to use less than the abovementioned minimum amount, while in other cases the upper limit mentioned must be exceeded. Where larger amounts are administered it can be advisable to divide these into several individual administrations over the course of the day. The same dosage range is envisaged for administration in human medicine. The other comments made above also apply, in a general sense.

The compounds of the present invention may be formulated into pharmaceutical compositions which comprise a compound according to the present invention in combination with a pharmaceutically acceptable non-toxic inert diluent or carrier. Possible forms for administration, in combination with various inert excipients, are tablets, capsules, powders, sprays, aqueous suspensions, injectable solutions, elixirs, syrups and the like. Such excipients include solid diluents or fillers, a sterile aqueous medium and also various non-toxic organic solvents and the like. Of course the tablets and the like considered for oral administration can be provided with a sweetener additive and the like. The therapeutically active compound should, in the abovementioned case, be present at a concentration of about 0.5 to 90 per cent by weight of the total mixture, that is to say in amounts which suffice to achieve the abovementioned dosage range.

In the case of oral use, tablets can of course also contain additives such as sodium citrate, calcium carbonate and dicalcium phosphate, together with various additional substances, such as starch, preferably potato starch and the like, and binders such as polyvinylpyrrolidone, gelatines and the like. Furthermore, lubricants such as magnesium stearate, sodium lauryl sulphate and talc can be conjointly used for tablet-making. In the case of aqueous suspensions and/or elixirs which are intended for oral uses, the active substance can be used together with various flavour-improving agents, dyestuffs and emulsifiers and/or together with diluents such as water, ethanol, propylene glycol or glycerine and similar compounds or combinations of this nature.

In the case of parenteral use, solutions of the active substances in sesame oil or groundnut oil or in aqueous propylene glycol of N,N-dimethylformamide can be employed, as can sterile aqueous solutions in the case of the water-soluble compounds. Such aqueous solutions should be buffered in the usual manner where required, and furthermore the liquid diluent should beforehand be rendered isotonic by addition of the requisite amount of salt or glucose. Such aqueous solutions are in particular suitable for intravenous, intramuscular and interperitoneal injections.

The manufacture of such sterile aqueous media is carried out in a known manner.

The compounds are used locally in the form of 0.5 to 5% strength, preferably 1% strength, solutions (for example in dimethylformamide, glycerine or water, alcohol such as ethanol and isopropanol, and buffer solutions), but also as emulsions, suspensions, powders and tablets.

In general, therefore, the invention also provides a pharmaceutical composition comprising as active ingredient at least one of the new active compounds in admixture with a pharmaceutically acceptable non-toxic inert solid or liquid diluent or carrier.

The invention further provides a medicament in unit dosage form comprising as active ingredient at least one of the new active compounds either alone or in admixture with a pharmaceutically acceptable non-toxic inert solid or liquid diluent or carrier. The medicament may include a protective envelope containing the active compound and, if used, the diluent or carrier.

The term "medicament in unit dosage form" as used in the present specification means a medicament as defined above in the form of discrete portions each containing a unit dose, or a multiple or sub-multiple of a unit dose of the active compound or compounds, especially a half, a third or a quarter of a unit dose, or two, three or four unit doses. Such portions may, for example, be in monolithic coherent form, such as tablets, suppositories, pills or dragees; in wrapped or concealed form, such as wrapped powders, cachets, sachets, or capsules; in ampoules, either free or as a sterile solution suitable for parenteral injection; or in any other form known to the art.

What is claimed is:

1. A pharmaceutical composition useful for treating mycotic infections in humans and animals which comprises an antimycotically effective amount of a compound of the formula:

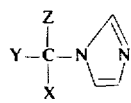

or a pharmaceutically acceptable non-toxic salt thereof, wherein

X is

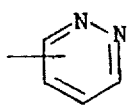 or 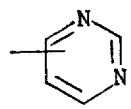

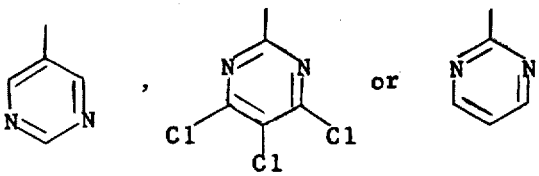

Y is phenyl or p-fluorophenyl, and
Z is phenyl,
in combination with a pharmaceutically acceptable non-toxic inert diluent or carrier.

2. A composition according to claim 1, wherein the compound is

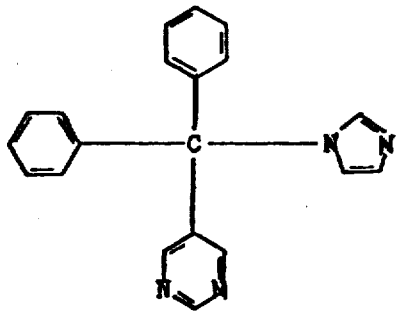

3. A composition according to claim 1, wherein the compound is

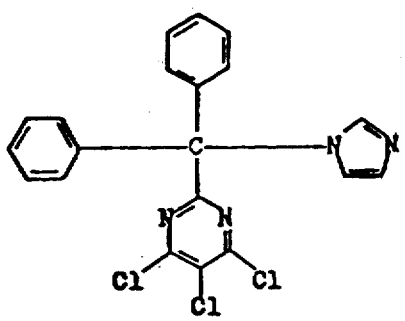

4. A composition according to claim 1, wherein the compound is

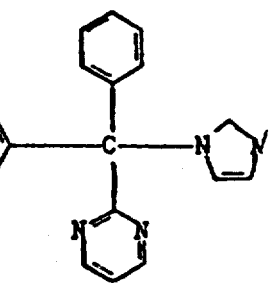

5. A pharmaceutical composition according to claim 1 wherein
X is

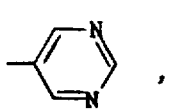,

Y is

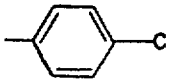

and Z is

.

6. A pharmaceutical composition according to claim 1 wherein
X is

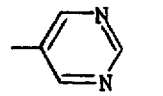,

Y is

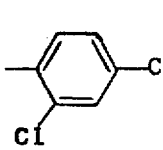

and Z is

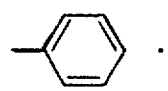.

7. A pharmaceutical composition according to claim 1 wherein
X is

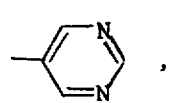,

Y is

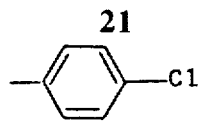

and Z is

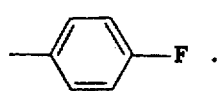

8. A pharmaceutical composition according to claim 1 wherein
X is

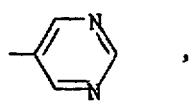

Y is

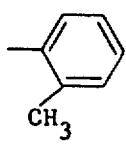

and Z is

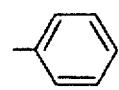

9. A method of treating mycotic infections in humans and animals which comprises administering to a human or animal in need thereof an antimycotically effective amount of a compound of the formula

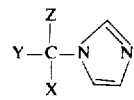

or a pharmaceutically acceptable non-toxic salt thereof, wherein X is

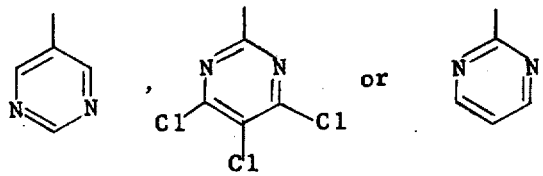

Y is phenyl or p-fluorophenyl, and Z is phenyl.

10. A method according to claim 9 wherein the compound is

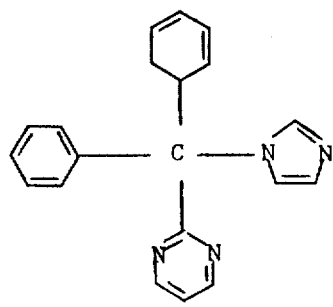

11. A method according to claim 9 wherein X is

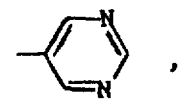

Y is

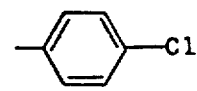

and Z is

12. A method according to claim 9 wherein X is

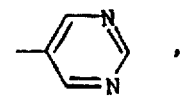

Y is

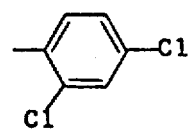

and Z is

13. A method according to claim 9 wherein X is

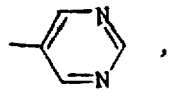

Y is

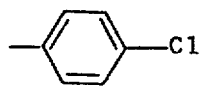

and Z is

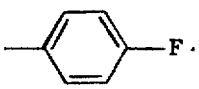

14. A method according to claim 9 wherein X is

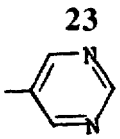
Y is
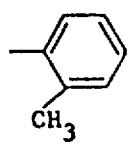
and Z is
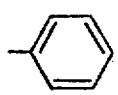
15. A method according to claim 9 wherein the compound is
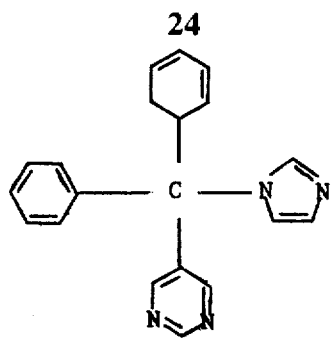
16. A method according to claim 9 wherein the compound is
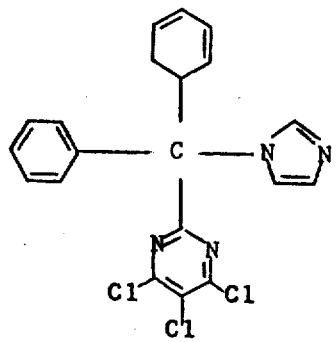
* * * * *

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

Claim 1 delete the following structural formulas:

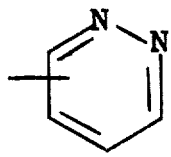 or 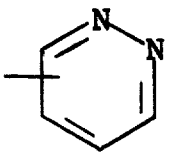

Claim 4 the structural formula should read:

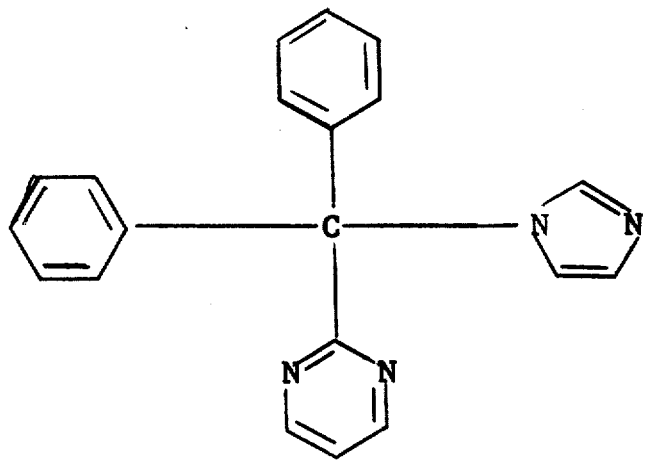

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

Claim 5 should read:

-- A pharmaceutical composition useful for treating mycotic infections in humans and animals which comprises an antimycotically effective amount of a compound of the formula:

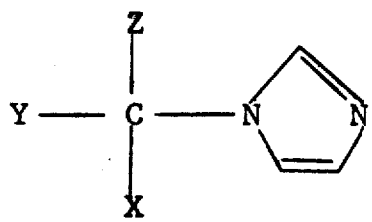

or a pharmaceutically acceptable non-toxic salt thereof, wherein

X is

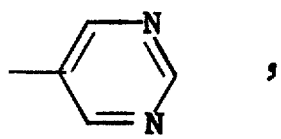,

Y is

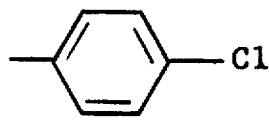

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

and Z is

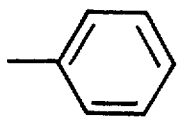

in combination with a pharmaceutically acceptable non-toxic inert diluent or carrier. --
Claim 6 should read:

-- A pharmaceutical composition useful for treating mycotic infections in humans and animals which comprises an antimycotically effective amount of a compound of the formula:

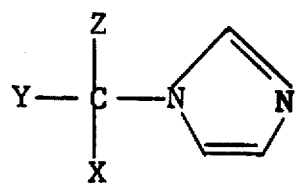

or a pharmaceutically acceptable non-toxic salt thereof, wherein

X is

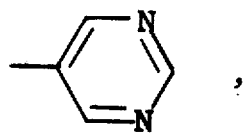

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

Y is

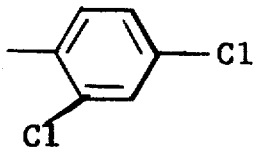

and Z is

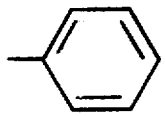

in combination with a pharmaceutically acceptable non-toxic inert diluent or carrier.--

Claim 7 should read:

-- A pharmaceutical composition useful for treating mycotic infections in humans and animals which comprises an antimycotically effective amount of a compound of the formula:

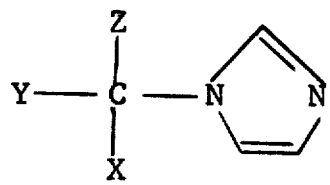

or a pharmaceutically acceptable non-toxic salt thereof, wherein

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

X is

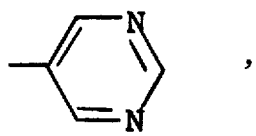

Y is

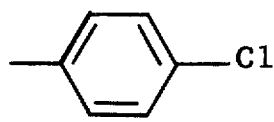

and Z is

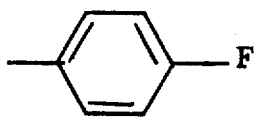

in combination with a pharmaceutically acceptable non-toxic inert diluent or carrier. --

Claim 8 should read:

-- A pharmaceutical composition useful for treating mycotic infections in humans and animals which comprises an antimycotically effective amount of a compound of the formula:

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

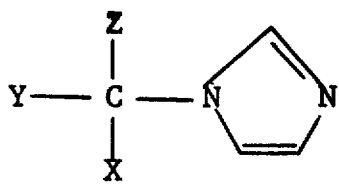

or a pharmaceutically acceptable non-toxic salt thereof, wherein

X is

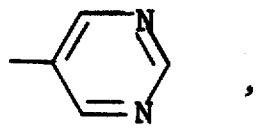 ,

Y is

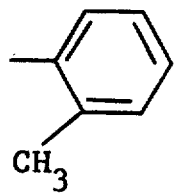

and Z is

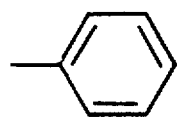

in combination with a pharmaceutically acceptable non-toxic inert diluent or carrier. --

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

Claim 11 should read:

A method of treating mycotic infections in humans and animals which comprises administering to a human or animal in need thereof an antimycotically effective amount of a compound of the formula

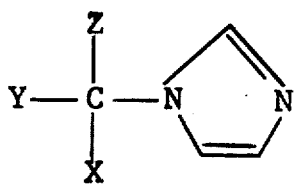

or a pharmaceutically acceptable non-toxic salt thereof, wherein

X is

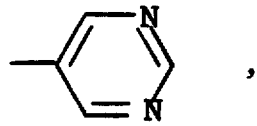  ,

Y is

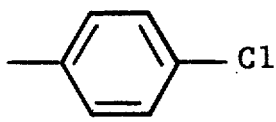

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

and Z is

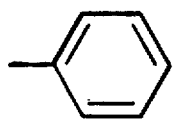

Claim 12 should read:

-- A method of treating mycotic infections in humans and animals which comprises administering to a human or animal in need thereof an antimycotically effective amount of a compound of the formula

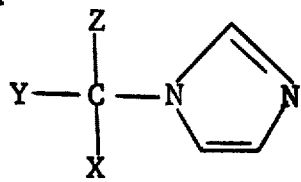

or a pharmaceutically acceptable non-toxic salt thereof, wherein

X is

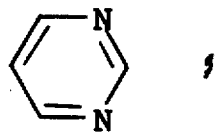

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

Y is

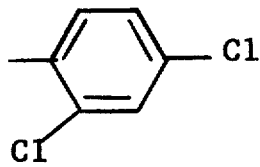

and Z is

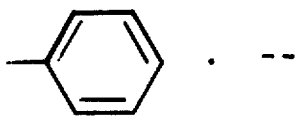

Claim 13 should read:

-- A method of treating mycotic infections in humans and animals which comprises administering to a human or animal in need thereof an antimycotically effective amount of a compound of the formula

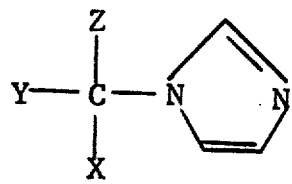

or a pharmaceutically acceptable non-toxic salt thereof, wherein

UNITED STATES PATENT OFFICE
CERTIFICATE OF CORRECTION

PATENT NO. : 3,934,014
DATED : January 20, 1976
INVENTOR(S) : WILFRIED DRABER ET AL It is certified that error appears in the above-identified patent and that said Letters Patent are hereby corrected as shown below:

X is

Y is

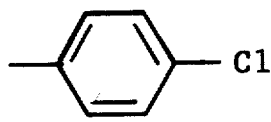

and Z is

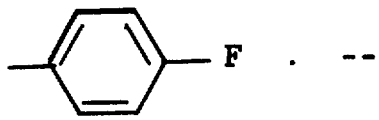

Claim 14 should read:

-- A method of treating mycotic infections in humans and animals which comprises administering to a human or animal in need thereof an antimycotically effective amount of a compound of the formula

UNITED STATES PATENT OFFICE
CERTIFICATE OF CORRECTION

PATENT NO. : 3,934,014
DATED : January 20, 1976
INVENTOR(S) : WILFRIED DRABER et al It is certified that error appears in the above-identified patent and that said Letters Patent are hereby corrected as shown below:

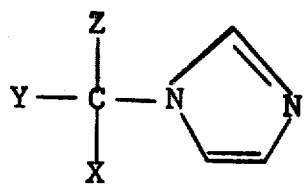

or a pharmaceutically acceptable non-toxic salt thereof, wherein

X is

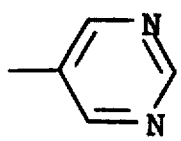

Y is

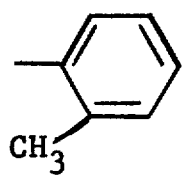

and Z is

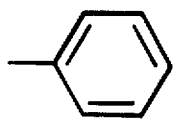

Signed and Sealed this

Thirty-first Day of August 1976

[SEAL]

Attest:

RUTH C. MASON
*Attesting Officer*

C. MARSHALL DANN
*Commissioner of Patents and Trademarks*